(12) United States Patent
Casaña Giner et al.

(10) Patent No.: US 9,006,145 B2
(45) Date of Patent: Apr. 14, 2015

(54) AGROCHEMICAL FORMULATIONS OF MICROCAPSULES FOR COMPOUNDS CONTAINING CARBOXAMIDE GROUPS

(76) Inventors: Victor Casaña Giner, Ebenfurth (ES); Miguel Gimeno Sierra, Berndorf (AT); Bárbara Gimeno Sierra, Berndorf (AT)

( * ) Notice: Subject to any disclaimer, the term of this patent is extended or adjusted under 35 U.S.C. 154(b) by 568 days.

(21) Appl. No.: 13/266,992

(22) PCT Filed: Apr. 30, 2009

(86) PCT No.: PCT/EP2009/003159
§ 371 (c)(1),
(2), (4) Date: Jan. 17, 2012

(87) PCT Pub. No.: WO2010/124705
PCT Pub. Date: Nov. 4, 2010

(65) Prior Publication Data
US 2012/0157315 A1    Jun. 21, 2012

(51) Int. Cl.
*A01N 25/28* (2006.01)
*A01N 47/36* (2006.01)
*A01N 47/28* (2006.01)
*A01N 47/34* (2006.01)
*A01N 37/24* (2006.01)
*A01N 43/32* (2006.01)
*A01N 43/40* (2006.01)
*A01N 43/56* (2006.01)
*A01N 43/78* (2006.01)
*A01N 47/38* (2006.01)

(52) U.S. Cl.
CPC .............. *A01N 25/28* (2013.01); *A01N 47/34* (2013.01); *A01N 47/28* (2013.01); *A01N 37/24* (2013.01); *A01N 43/32* (2013.01); *A01N 43/40* (2013.01); *A01N 43/56* (2013.01); *A01N 43/78* (2013.01); *A01N 47/36* (2013.01); *A01N 47/38* (2013.01)

(58) Field of Classification Search
CPC ... A01N 25/28; A01N 43/40; A01N 2300/00; A01N 37/24; A01N 43/32; A01N 43/56; A01N 43/78; A01N 47/36; A01N 47/38; A01N 25/04
See application file for complete search history.

(56) References Cited

U.S. PATENT DOCUMENTS 4,640,709 A * 2/1987 Beestman ................ 504/300
5,160,529 A   11/1992 Scher et al.

FOREIGN PATENT DOCUMENTS

| WO | WO9213448 | 8/1992 |
| WO | WO2004016234 | 2/2004 |
| WO | WO 2006092409 A2 * | 9/2006 |
| WO | WO 2007112933 A1 * | 10/2007 |

OTHER PUBLICATIONS

Wermuth, Drug Discovery Today, 2006, 11(7/8), 348-354.*
Merriam-Webster Online Dictionary, obtained online at: www.merriam-webster.com, downloaded on Jul. 5, 2008.*
International Search Report issued in connection with International Patent Application No. PCT/EP2009/003159, completed Jan. 19, 2010, mailed Feb. 2, 2010, 3 pages.
Written Opinion of the International Searching Authority issued in connection with International Patent Application No. PCT/EP2009/003159, mailed Feb. 2, 2010, 7 pages.

* cited by examiner

*Primary Examiner* — Abigail Fisher
(74) *Attorney, Agent, or Firm* — Vedder Price PC

(57) ABSTRACT

The present invention is directed towards microcapsules, uses and methods of microencapsulation with improved properties regarding agglomeration, bleeding and control of the reaction. The invention is especially suitable for chemical compounds with at least one carboxamide group, preferably for microencapsulation of those compounds wherein the carbonyl group is attached to a nitrogen atom or nitrogenated heterocycle and wherein the microencapsulation reaction may be too vigorous. The microcapsules are characterized by a mixed glycoluril-polyurea polymer wall, wherein the polyurea groups come from a urea-formaldehyde resin and not from isocyanate monomers or prepolymers. The process of making such microcapsules a dispersant in the oil phase of the type of block copolymer of vinylpyrrolidone/vinylalkene and/or vinylpyrrolidone/vinyl acetate and the microencapsulation reaction may be carried out without the presence of any polyamine/polyol acting as a catalyst.

11 Claims, No Drawings

AGROCHEMICAL FORMULATIONS OF MICROCAPSULES FOR COMPOUNDS CONTAINING CARBOXAMIDE GROUPS

The present invention, as the title indicates, consists in microcapsules, uses and method of microencapsulation with improved properties regarding agglomeration, bleeding and control of the reaction. The invention is especially suitable for chemical compounds with at least one carboxamide group, preferably for microencapsulation of those compounds wherein the carbonyl group is attached to a nitrogen atom or nitrogenated heterocycle and wherein the microencapsulation reaction may be too vigorous. The microcapsules are characterized in that their wall contains a mixed polymer glycoluril-polyurea, wherein the polyurea groups come from a urea-formaldehyde resin and not from isocyanates in the form of monomers or prepolymers, being used in the process of making such microcapsules a dispersant in the oil phase of the type of block copolymer of vinylpyrrolidone/vinylalkene and/or vinylpyrrolidone/vinyl acetate and the microencapsulation reaction may be carried out without the presence of any polyamine/polyol acting as catalyst of the reaction of polyurea/polyurethane as it is the prior art.

BACKGROUND OF THE INVENTION

The technique of microencapsulation by means of polymerization of Isocyanates, for its use in several fields, including agriculture is very well known for the formulation chemist. Many patents describe microencapsulation by means of isocyanates, prepolymers of isocyanates, urea-formaldehyde resins with polyols and functionalized amines as catalysts. The applicant, as described in EP 1840145 introduced in the wall forming materials of the microcapsules, for the first time, derivatives of glycoluril combined with aliphatic and aromatic isocyanates. That patent, that reflects the closest state of the art of the present invention (of the same inventors), shows a method of microencapsulation in which, in between other novel elements and advantages, the microcapsules have improved properties regarding the better control on the chemical structure of the wall (due to the introduction of glycoluril derivatives) and improves the toxicology associated to production, due to the fact that partly the isocyanates are substituted by the less toxic glycoluril derivatives and the quantity of isocyanates is lower.

In the same way, due to the lower reactivity of the glycoluril derivatives, the microencapsulation reaction described in EP 1840145 is easily controlled with respect to the state of the art prior to EP. The present invention improves the formulated products resulting from the invention EP 1840145, with regard to several compounds, and it is novel in the present invention the combination of glycoluril resins with urea resins, without using catalysts of the type metal dibutyl-laureates or amines or polyols. At the same time, in the present invention we use a determined type of surface active agents that improves notably the stability at long term, while this combinations are clearly non obvious in front of any prior art known by the authors at the view of the almost infinite combinations possible to be made of polymers or oligomers or monomers that are wall forming materials, and at the same time that during the process, a determined type of surface active agent is used in order to obtain a good emulsion that yields a mean particle size lower than 5-6 pm, and moreover, improves the properties of the final formulation in which such microcapsules are contained regarding agglomeration and bleeding, as this is the effect of the surface active agent CoP-1 described elsewhere in this document.

The inventors of the present invention have continued to research in processes with better control of reaction since the realization of the invention EP 1840145. It must be noted that an industrial microencapsulation reaction is an "all or nothing" reaction, namely, that if a phase inversion takes place, or the particle size is not appropriate, the whole production lot (e.g. 500 to 20000 kg) must be sent to waste, with the losses of the materials used in such reaction and the costs of waste-burning. Then, small advances in the control of reaction have a high economical impact, since such advances may reduce the percentage of failed miroencapsulations' reactions from 0.5% to a 0.1%, with a high economical impact. This is the case of the present applicant: the inventors have observed in their pilot plant (of 50 kg per batch) during 2 months such mentioned reduction in failed reactions -for several compounds to be microencapsulated-, that reduction of failures due to change the method described in EP 1840145 to the method described in the present invention. Together with this improved control of reaction, the present invention improves (with regard EP 1840145 and all microencapsulation processes published or patented known for the inventors) another problem than may occur as is the bleeding and the agglomeration of microcapsules. The latter improvement over the prior art is specially relevant for the shelf-life of formulated product at long term.

Among the problems that may appear in formulations containing microcapsules is the appearance over time of a phase separation (a part of the oil used during the process is separated as a layer on the top of the external water phase of the microcapsules), generally known as "bleeding", as well as problems associated with the agglomeration of the microcapsules over time. The present invention deals with formulation of microcapsules that are improved with respect other ones, for periods over two years, In terms of bleeding and agglomeration, apart from the improvement in the control of the reaction due to the use of polyurea "blocks" as wall forming materials (combined with glycoluril resins) instead of the use of the initial use in the reaction of isocyanates in monomer, oligomer (prepolymers) isocyanates, as is the state of the art.

Another problem not solved by the state of art is the optimization of the microencapsulation process in reference to the ability to control the speed of reaction in those cases wherein compounds may intervene in the formation of the polyurea wall during the microencapsulation reaction, in particular compounds having groups R—CO—N—R' being R and R' any moiety), as it is the case for the agrochemical compounds with carboxamide groups. While EP 1840145 provides an improvement in this respect (by using less reactive glycoluril compounds compared) over the prior art of EP 1840145, in the present invention one of the improvements is that we combine specifically a certain type of wall forming materials and a dispersant/surfactant (surface active material) of the type CoP-1 to create microcapsules for the special case of compounds with at least a carboxamide group, as is the case of sulfonylureas and other agrochemicals. For this compounds with carboxamide groups, it is observed that by the use of the present invention, we obtain the benefits of incorporating glycoluril groups to the polyurea wall (being this polyurea the result of the reaction of urea-formaldehyde resin and not with isocyanates as is the case in EP 1840145) and at the same time we obtain a better control of the reaction (apart from improving the bleeding and agglomeration characteristics of the formulated carboxamides). It is noted that EP 1840145 it can also be prepared formulations of compounds with carboxamide groups; however in two reactions in an industrial reactor of 200 liters happened an overheating and rapid evolution of $CO_2$ with consequent loss of emulsified phase due to spilling from the top of the reactor. While this problem may be solved by a different design in the reactor (to allow the elimination of the $CO_2$ by a more efficient way), in the present invention, the inventors have sought a solution that goes beyond an obvious solution for this problem. At the end, the present invention has resulted in surprising benefits over those faced by the inventors, and provides a microencapsulation process and microcapsules wherein the reaction is better controlled and further, the properties of the formulation (regarding bleeding and agglomeration at long term) are improved, and also the invention may be used for compounds that do not have carboxamide groups (since the improved properties of the formulation still apply). Although the problem that lead the inventors to invent the present invention had its origin in the microencapsulation of boscalid and then prochloraz, we have found that the invention may be applicable to other compounds without carboxamide groups, although it is declared that the best improvement (but not the only one) is referred to the control of the reaction for carboxamide groups.

Noteworthy, the present invention is perfectly applicable for any Industrial field in which carboxamide compounds are to be microencapsulated, as might be flame retardants, phase transfer materials, pharmaceuticals, cosmetics, etc. We refer hereinafter to the field in which we have our most interest, namely, in the agrochemical field.

DESCRIPTION OF THE INVENTION

The way in which we obtain the desired result according this invention is dual:

1) On one hand, the necessary use of at least a copolymer [CoP-1] selected from the groups:
   a. N-vynil-2-pyrrolidone combined with vinyl-1-alkenes (preferably 1-butene) or polymers of 1-alkene-N-vynilpyrrolidone. The CAS No. when the alkene is 1-butene combined with N-vynil-2-pyrrolidone is #[26160-96-3]. The commercial products corresponding to this group are of the type Ganex® or Agrimer® AL
   b. N-viyl-2-pyrrolidone combined with vinyl esters, preferably vinyl acetate. The CAS No. in this case is #[25086-89-9], preferably the commercial product Agrimer® VA 3, 5 or 6.
   The compounds 1) a. and 1) b. have a notable effect on the bleeding and the agglomeration. Below 0.5% wt.-% of 1) a. +1) b. there is observed no positive effect on bleeding and agglomeration of microcapsules. Above a presence at 15% wt.-% it is compromised the room for other appropriate coformulants needed for the microencapsulation and/or the finished formulated product and also the quantity of water necessary to obtain a product with an acceptable viscosity.
   In addition to this, it has been observed that the presence of lignosulfonates (derivatives of lignosulfonic acids) helps, more than for the stability at long term, in a faster dispersion of the microcapsules, in the case of the moment when the farmer dilutes the concentrated microencapsulation in the spray tank in the field prior to application in the crop.
2) On the other hand, the combined use of wall forming materials [WF-2] of:
   a. A urea-formaldehyde resin, preferably with a CAS No. #[9011-05-6], and more preferably to those corresponding to the chemical structure of the product UFR® 80
   b. A glycoluril resin of the type N,N',N",N"'-tetrakis (alkoxyalkyl)glycoluril, or one with 1 or 2 free hydroxyl groups as N,N'-bis(alkoxyalkyl)glycoluril or N,N',N"-tris(alkokyalkyl)glycoluril, preferably corresponding with the CAS No. #[15968-37-3], and preferably those corresponding with the chemical structure of Cymel® 4040 and their oligomers (namely, monomers and oligomers with 2 to 10 mols of tetrakis(butoxymethyl)glycoluril.
   The products 2) a. and 2) b. have a marked effect in the reduction of to fast or too violent reactions during the formation of the microcapsule's wall (polymerization). The concentration of 2) a. +2) b. with respect to the final microencapsulated formulation is normally 0.5-7.5% wt.-%.
3) Additionally, we restrict the mean particle size of the microcapsules to 1-6 μm, since for values over 6 μm and with the materials named in 2), the agglomeration is increased, and below a mean size of 1 μm, the microcpaules need a so high stirring speed that part of the active compound (e.g. the agrochemical to be microencapsulated) because is (partially) expelled from the oil droplets, goes to the water phase, resulting in crystals in the final formulation (namely, not all the active ingredient is microencapsulated). In this sense, apart from the necessary use of the compounds 1) a. or 1) b., the use of dispersants soluble in oil is very encouraged. In particular, are preferred those of the type block copolymer A-B-A of polyethylenglycol and fatty acid of long chain (over 12 carbons) functionalized at least in one position, preferably by an hydroxyl group. We cite this explicit type because is one of the few readily available oil soluble dispersants, not reactive and of low cost, and not because we disregard other dispersants that have the same function. The range 1-6 μm belongs to the state of the art of microencapsulated formulations, but it is not state of the art that this range is especially superior to other ranges for the microcapsules described in the present invention.

Commercial products belonging to 1) a. are known, as in a non-limiting way:

Agrimer AL 10; Agrimer AL 10LC; Agrimer AL 25; Ganex P 904; Ganex P 904L; Ganex P 904LC.

Commercial products belonging to 1) b. are known, as in a non-limiting way:

Agrimer VA 03E; Agrimer VA 05E; Agrimer VA 07E; Agrimer VA 3; Agrimer VA 5; Agrimer VA 6; Agrimer VA 7W; Copolyvidon; Copolyvidonum; E 335; E 535; E 635; E 735; Eukaline 480; GAF-E 735; GAF-S 630; Ganex E 535; Gantron PVP; Gantron S 630; Gantron S 860; I 335; I 535; I 635; I 735; Kolima 10; Kolima 35; Kolima 75; Kollidon VA 64; Luviskol 64; Luviskol 64W; Luviskol 73E; Luviskol 73W; Luviskol VA 28E; Luviskol VA 281; Luviskol VA 37; Luviskol VA 37E; Luviskol VA 37E60; Luviskol VA 37HM; Luviskol VA 371; Luviskol VA 55; Luviskol VA 55E; Luviskol VA 551; Luviskol VA 64; Luviskol VA 64P; Luviskol VA 64W; Luviskol VA 73; Luviskol VA 73E; Luviskol VA 73W; Luviskol VA-HM; Luviskol VAP 37; Luviskol VAP 73; Luvitec VA 64; Luvitec VA 64W; NSC 114023; NSC 114024; NSC 114025; NSC 114026; P 0382; P 0385; PVA 6450; PVP-VA; PVP-VA-E 735; PVP-VA-W 735; PVP/VA 630; PVP/VA E 335; PVP/VA E 535; PVP/VA-S 630; PVP/VA-S 630L; PVPNA-S 630; PVPVA 64; PVPVA 7/30; Plasdone S 630; Polectron 845; R 219; S 630; VA 64.

Commercial products belonging to 2) a. are known, as in a non-limiting way:

113E1; 12C257A; 1708; 3T/3TS; A 2; A 2 (aminoplast); AL 3029; AL 3029R; Acrisin FS 017; Aerolite 300; Aerolite A 300; Aerolite FFD; Aerolite UL 333; Agroform; Amikol 65; Amres 255; Anaflex; Antimnol WMS; Arbocoll FK; BASF 285; BASF 570; BB 032; BC 20; BC 40; BC 40 (polymer); BC 70; BC 77; BE 382; BT 970; BTLU-RW 25; BU 286; Bakelite UA 125; Basopor 293; Beckamine 21-500; Beckamine 21-510; Beckamine 21-511; Beckamine G 1850; Beckamine J 300S; Beckamine N 113; Beckamine N 117T; Beckamine N 80; Beckamine NF 5; Beckamine P 136; Beckamine P 138; Beckamine P 138-60; Beckamine P 196; Beckamine P 196M; Beckrol G 1850; Beetle 1050-10; Beetle 1052-8; Beetle 1074; Beetle 212-9; Beetle 216-10; Beetle 55; Beetle 60; Beetle 65; Beetle 7238; Beetle 7238-20; Beetle 80; Beetle BE 610; Beetle BE 655; Beetle BE 665; Beetle BE 678; Beetle BE 685; Beetle BT 322; Beetle Bu 700; Beetle GXT-UF-A 10; Beetle Resin BT 322; Beetle UFR 80; Beetle XB 1050; Borden UL 96; Bu 700; Budamin KE 60B; C 3; C-TH 39; CAR 54; CBU-UF; CR 2664; CR 583; CU 1328C10K; CU 1500G; CU-A; CU-A (aminoplast); Capture; Carbamol; Carbamol 2M; Carbomol MT 2; Cargill 2052; Cargill 2148; Cascamite 151S; Casco 5H; Casco C 511X; Casco FG 345; Casco PR 145; Casco PR 247; Casco PR 274; Casco PR 335; Casco PR 356; Casco Resin 520HT; Casco Resin 600; Casco Resin C 802B; Casco Resin FG 345; Casco Resin FG 486; Casco UL 30; Casco UL 53; Casco WS 114-79; Casco WS 138-43; Casco WS 138-44; Cascorit 1201; Cascorit 1209; Cascorit 1250; Cascorit 1352; Catalure; ChemBond; Chembond YTT 063-02; Chemoform A; Chemoform P; Crosrez; Cymel 3717; Cymel U 64; Cymel U 80; Cymel UFR 60; Cymel UFR 65; Cymel UM 15; DM; Depremol DT; Depremol M; Diaform UR; Diakol 14; Diakol 3T; Diakol DM; Diakol F; Diakol M; Diakol M 1; Diakol S; Diakolin; Ducol FM; Ducol M; Dukol; Dukol A; Dukol E; Dukol EP; Dukol K; Dukol M; Dukol MA; Dukol MD; Dukol MS; Dukol MU; Dukol S; Duracet 827; Durite AL 3029C; Durite AL 8405C; Dynea 246; Dynomin UI 16; Dynomin UIX 27; Dynomin UM 15; Dynorit L 101; Dynorit L 166; E 2; EMG; EU 40; Eibond UL 3201S; Epok U 9048; FAN; FG 413; FG 458; FG 472; FG 486D; FG 515; FM 17; FM 17-1; FN 16B; Fibraset TC; Foramin PB 118; Formol S; Formurea 80; Forpap K 2; Fudowlite U; GP 2997; GP 403D23; GP 487D39; GP 487E45; GPX-J 1-6; Gabrite; HB 21; HD 1015; HR 930; HR 930 (aminoplast); Hiacoll 4780; Hiacoll H 25H; Hiacoll H 67; Hiacoll UF; Hicofor AC; Hygromull; IRSA 848S; Igetaleim UA 105; Igetaleim UA 125; Igetalelm UN 105; Insta-Bond R 101A; Iporka; Irgasol HTW; JT; K 0; K 17; K 27; K 350; K 350 (polymer); K 385; K 385 (urea resin); K 385/67; K 411-02; K 411-O2sb; K 8811; K 8870; K 8886; KF 0; KF 01.5; KF 02; KF 312; KF-A; KF-B; KF-BZh; KF-ES; KF-MG; KF-MT; KF-MT 15; KF-MT(N); KF-MT-F; KF-N 54; KF-NFP; KF-NV; KF-O; KF-PR; KF-Zh; KF-Zh(M); KFK 20; KFMP 15; KFP; KFP (aminoplast); KFPC 2; KFS 01MUU; KFS 1; KFS 312; KFS 78; KM 2; KS; KS (urea resin); KS 11; KS 35; KS 68; KS 68A; KS 68B; KS 68M; KS-B 40Zh10M; KS-M 0.3P; KS-MO 3SVL; Karbadur; Karbadur A; Karbamet T; Karbamol; Karbamol M 2; Karbamol MT 2; Karbamol b/m; Kauresin K 244; Kaurit 210; Kaurit 270; Kaurit 285; Kaurit 285fl; Kaurit 350; Kaurit 385; Kaurit 407; Kaurit 420; Kaurit 471; Kaurit S; Kaurit WHK; Kauritec 305; Knittex TC; Knittex TS; Koprez 87-110; Krepitel M 2; Kymene 435; L 195; L 311; LF 1; LF 20; LF 25; LP; LP (aminoplast); LPR; Laropal A 101; Lendur; Leuna 4545; Leuna 5554; Leuna-Leim 1310; M 19-62; M 3; M 60; M 60 (formaldehyde polymer); M 70; MCh 13; MCh 52; MF; MF 1; MF 17; MF 27; MF resin; MF-Zh; MFP; MFP 1; MFP 2; MFP 3; MFP 4; MFPS 1; MFPS 2; MFS; MKh 52; MM 54V; MN 15; MPF 2; MS 10; MS 10 (polymer); MX 202; MX 290; Melan 11; Melan 11E; Methex 40; Methylene-N,N'-bis(hydroxymethyl) urea polymer; Methylolurea resin; Metoksol K 1; Micrea; Micrea DZ; Mirbane SU 118K; Moform; Moform 50; Mouldrite A 256; Mybond 590; N 122; N 50; N 50 (aminoplast); N 8314; NQTRH; NST 002; NST 201; Nationallite A; Neste 3675; Neste 5486; Nikalac MS 20U; Nikalac MX 201; Nikalac MX 280; Nikalac MX 290; Nikalac N 2009; Nitroform; Nitroform (aminoplast); Nitroform Blue Chip; Noxylin; Nutralene; ON 1289; OpoIan UR 3; Oshika 104; Oxymetylurea; P 196-60; PKF 1; PKP 52; PKS 0; PL 117; PL 2C; PMF; PMF (aminoplast); PR 703-78; PT 22; Penoizol; Pergopack M 3; Pergopak 4210; Pergopak M; Pergopak M 2; Pergopak M 3; Pergopak M 4; Permafresh 479; Pianizol; Piatherm; Piatherm D; Placol; Plastopal BT; Plastopal F; Plyamine HD 1129A; Plyamine P 364BL; Plyamine TD 2712; Polyfix LF 20; Polyfix UC 30M; Polyfix UC 32M; Polynoxylin; Polynoxyline; Polyresin MFB; Ponoxylan; Prefere 87-1640H; Pressamine 031; Pressamine 210; Pressamine 233; Protesine M 160; RN 512; RUUI 458T95; Resamin 155F; Resamin HF 180; Resamin HF 227; Resamin HW 505; Resamin HW 864; Resimene 933; Resimene 970; Resimene 975; Resimene 980; Resimene U 915; Resimene U 975; Resimene X 918; Resimene X 970; Resimene X 975; Resimene X 980; Resin 5601; Resina X; Resitop UL 3201; Resurpa RP 306; Riken Resin B 85; Riken Resin UP; Rollex 50; Rousselot 41-22; S 40; S 40 (aminoplast); S-Resin AER 20; S-Resin SB 90; S-Resin SC 1; S-Resin SE-N; SF 30-7N; SFK 70; SK 75; SK 75V; SKF-NM; SU 100; SVS; SVS (polymer); Sadecol L 3096; Senocoil GP 474; Silekol; Silekol FO; Silekol L 2; Silekol M; Silekol M 1; Silekol M 2; Silekol MZ; Silekol S; Silekol S 1; Silekol SE; Silekol W 1; Sobral P 138X; Struct-Bond C 3; Suisobond 5031; Sumirez 614; Sumitex 250; Sumitex 260; Sumitex 800K; Sumitex 810; Sumitex H 90; Sumitex NF 113; Sumitex Resin 250 Conc; Sumitex Resin 810; Super-Beckamine P 138; Sylvic DUO-A 110; Synteko 1360; T 101; TA 100; TA 21; TC 138; TL 200; TUF; TX 202; Tesazin 3000-60; Tesazin 3002-60; Tesazin 3003-60; Thermotite 3HSP; Thermotite 8HSP; U 310; U 70; U 701; U 726; U 755; U 756; U 80; U 963; U-Lite; U-Lite IG 33; U-Loid 100; U-Loid 22; U-Loid 301; U-Loid 320; U-Loid 555; U-Loid 701; U-Loid 730; U-Loid 755; U-Loid 755S; U-Loid NV 555; U-Loid S 22; U-Loid S 50; U-Loid UL 310; U-Loid UL 320; U-Pearl C 120; U-Pearl C 122; U-Pearl C 122R; U-Pearl C 125; U-Pearl C 22; U-Pearl I; U-Pearl S 122; U-Ramin P 1400; U-Ramin T 101.; U-Ramin T 105; U-Ramin TSL 58; U-Van 10HV; U-Van 10R; U-Van 10S; U-Van 10S60; U-Van 11HV; UA 105; UA 125; UA 125-05; UA 126-46; UA 133; UA 143; UA 909; UB 104; UC 120; UF 240; UF 33; UF 85; UF resin; UFP 1001; UFR 300; UFR 60; UFR 65; UFR 80; UFR 652; UKS; UKS 11; UKS 72; UKS 73; UKS-A; UKS-B; UL 002; UL 013; UL 52R; UL 96; UM-G; US 6200; UST; UW 061; UW 062; UW 072; Uformite 700; Uformite F 240; Uformite F 240N; Umacol C; Umacol CM; Umacol CMR; Umalur; Uralite; Uralite (polymer); Uramex U 165; Uramite; Ureapap; Ureapap W; Urecoll 135; Urecoll 181; Urecoll A; Urecoll K; Urecoll KL; Urecoll S; Urecoll TS; Urelit C; Urelit HM; Urelit P; Urelit R; Urepret; Urex 3273; Urex 328; Urezit 340; Urezit 51; Urofix; Urofoam; Urofoam R 101; VF Filler; VK 1M; VPS-G; Varcum 404B;

Veganit; Viamin HF 164; Viopret TR; Virset A 125; W 300; W 436; W 70; WC 10; WF 11SCAV500; WQ-II; WW 856; X 104; Xilocolla L 1570; Yuri UC 120Y; Yuri UN 811; Yuri UN 821W; Yuri UN 827W.

Commercial products belonging to 2) b. are known, as in a non-limiting way:

Cymel 1170; E 2403; Tetrakis(butoxymethyl)glycoluril, N,N',N",N'"-tetrakis(alkoxlalkyl)glycoluril Commercial products belonging to 3) are known, as in a non-limiting way:

Dispersant of the Atlox series, in particular Atlox 4912.

It must be noted that the products mentioned above are (mostly) registered trademarks and names used in the commerce.

The carboxamide-containing compounds referred in the agrochemical application of the present invention correspond, among others to: boscalid, prochloraz, carboxin, fenfuram, flutolanil, furametpyr, mepronil, oxycarboxin y thifluzamide (common names ISO and/or ANSI) as well as sulfonylureas. The use of this compounds in the process of this invention (and the resulting microcapsules thereof) yield characteristics referred to bleeding and agglomeration clearly superior to the state of the art, and particularly, improved with respect of EP 1840145 (in such case specially also with respect control of reaction, temperature increase and speed of evolution of $CO_2$).

A particular case occurs when the carbonyl group of the carboxamide is bound to a heterocycle by means of a bond with a nitrogen of the heterocycle. In this case, what is observed by the use of the selected compounds 1) and 2) (respectively a. and b. in both cases) is the total absence of vigorous reactions with high speed of evolution of $CO_2$ (must be noted that the formation of a polyure wall implies the reaction with water and evolution of $CO_2$, that may suppose great problems for those reactors not specially designed for a fast evacuation of that gas, or in formation of foam that escapes through the open part of the reactor). Particular compounds appropriate for the embodiment of the invention are boscalid and prochloraz, since we have observed that with state of the art wall forming materials, the reaction is vigorous with excessive increase of temperature and rapid evolution of $CO_2$.

Without having a strong theoretical explanation, we believe that the carboxamide groups of the named pesticides act somehow as catalysts and reacting in part with the wall forming materials, through the group R—N—CO—R'. It is also possible that due to the unavoidable use of pesticide's technical material (namely, not with pure pesticides, rather with a level of impurities of 0.2-10%) this technical material—and due to the presence of carboxamide groups—has impurities in which the carboxamide group is free to react (or initiate or accelerate) the reaction with the isocyanate groups in the presence of water. It seems that in the case of prochloraz, the present of a particular moiety R- (it is an imidazol bound to a nitrogen to the carboxamide group) this reaction is more appreciable than with other pesticides mentioned. Although not proven experimentally, it is very reasonable to think at the view of its chemical structure, that the present invention is of great interest in the microencapsulation of sulfonylureas, since they have groups R—N—C═O—N'. In any case, our observations, whatever the chemical reasons implied in the reaction, show that for the microencapsulation of agrochemicals with carboxamide groups, the use of the polymers (as surface active agents) and the wall forming materials as already explained, have evident advantages.

DETAILED DESCRIPTION OF THE INVENTION

Our objective is to obtain a formulation (of pesticide compounds that contain as active ingredient at least a compound with at least a carboxamide group) containing microcapsules by means of a mild process (with respect to temperature increase and $CO_2$ evolution) that moreover do not show agglomeration either bleeding at long term storage.

For this purpose the following process steps are performed:

I) A water phase is prepared containing:

I.A) A solution of polymer CoP-1 in water (at 1-60%, always in wt.-% unless stated otherwise) present in 50-60 parts, preferably 30-40 parts (a quantity of 1-15% in the total formulation in dry weight of CoP-1)

I.B) A hydrocolloid solution of polyvinyl alcohol (or similar)—at 5-30% in water—and/or biological gums (xanthan gum, Arabic gum, guar gum, etc.) present in 1-15 parts, preferably 2-10 parts I.C) One or more surfactants soluble or dispersible in water (that allow the later emulsification of the oil phase in the water phase) present in 1-10 parts, preferably 2-5 parts. A special emulsifier for doing the emulsion and to obtain a reduced particle size are the block coplymers ethoxylated/propoxylated (much more effective if they are only ethoxylated or only propoxylated)

I.D) A catalyst of the polymerization reaction suitable for the compounds WF-2, 2) a. and b., preferably para-toluensulfonic acid (p-TSA), for the reaction of the glycoluril compounds and optionally amines, polyamines, functionalized polyamines, polyols, in order that they help in the reaction of the urea resins. One of the distinctive aspects of the present invention is that it is not necessary the use of an amine or a polyol for the formation of the polyurea groups, rather, in our process, we use the own reactivity of the wall forming materials urea resins with water for autocatalysis. This way the reaction is better controlled and slowe, apart from being absolutely novel this combination of catalysts and reactants for the formation of the microcapsule's wall.

I.E) Optionally other coformulants, among them it is recommended emulsifiers and/or dispersants (for the correct emulsification performed by the farmer in the spray tank), pH adjusters (e.g., phosphoric acid, ascorbic acid, in the amount needed to reach the pH in which the reaction takes place [pH=4-6, normally], with due account of any other catalyst that may be present), antifoam, antimicrobians, antioxidants and UV protectors. The compounds I.E) normally should not be over 5 parts in the formulation. It is understood that any coformulant type used in agrochemical formulations may be included in this section (e.g., anticrystallizants, antifreezing agents, viscosity modifiers, emetics, etc.)

II) An oil phase is prepared containing:

II.A) At least an active ingredient (a.i.) of the agrochemical formulation that we wish to prepare. If It is only one a.i., then it must be a carboxamide containing compounds, if there are several a.i., then, for the best profit of the invention it is convenient that at least one a.i. is containing at least a carboxamide group. The adequate quantity if 1-50 parts II.B) If the a.i. (or mixture of a.i.) is a solid product (at a temperature above the initial temperature for emulsification) it is very convenient that a solvent is used, in order to get a good emulsification of the a.i. Any unpolar or slightly polar—but not miscible in water—solvent used in agriculture is adequate, and must be present in the needed amount to solubilize the a.I. (or slightly above, e.g., 50% above the quantity needed for solubilization)

II.C) A wall forming material of the type glycoluril resin (corresponding to WF-2, II) b.) at 0.1-5 parts and a wall forming material of the type urea-formaldehyde condensate (corresponding to WF-2 II) a.) at 0.1-7 parts II.D) At least a compound with surface activity (dispersant and/or emulsifier) that is oil soluble, at 0.1-5 parts, preferably a Block copolymer ABA as described in 3) above.

II.E) Optionally coformulants as mentioned in I.E), or those that necessarily must be solubilized in the oil phase. It is understood that any coformulant state of the art for agrochemical formulations may be included in this section (e.g., UV or visible light protectors, antioxidants, etc.). Normally, compounds II.E) must not be over 5 parts.

Once the two phases are prepared (water and oil) they are heated to 40-90° C. Once reached the temperature necessary for the reaction to take place (recommended 60-70° C.) it is introduced the oil phase II) in the water phase I) and is vigorously stirred, e.g. at 2500 rpm by means of any state of the art stirrer appropriate to emulsify. After the emulsification step (normally it takes 1-15 minutes, depending the size of the reactor and the speed/geometry of the stirrer) the abovementioned stirrer is changed to another that provides much lower shear stress, e.g. anchor stirrer, and the speed is reduced to about 200 rpm.

Finally, to the resulting suspension of microcapsules it Is added the pH modifiers (e.g., sodium carbonate or citric acid in order that a pH is reached (and the formulation itself) in which the stability is optimal), viscosity modifiers (preferably aluminosilicates and/or micronized clays, bentonites, zeolites, sepiolites and any other inert compound -both for the a.i. and for the functionality of the formulation—and water as desired to reach the desired concentration of a.i. for the commercialization of the formulation.

It is considered that the formulation reaches its sufficient quality degree (namely, satisfies the needs of the farmer) when the content of the a.i. (or several a.i., normally a.i. designates singular or plural) is present In similar commercial products or their chemical equivalents, and such formulation Is used in the normal way in that the farmer uses.

For the correct reproduction of the invention the following tips must be considered:

1. The quantity of a.i. must be lower than the limit of emulsification in water with the appropriate emulsifiers and at the kinetic speed recommended (1500-5000 rpm, preferably about 2500 rpm) during the emulsification process—
2. The emulsifiers of first choice for the water phase, in the amounts previously cited, must be block copolymers ethoxylated/propoxylated, as those represented by CAS No. #[106392-12-5] and/or block copolymers of 2-methyl propenoic acid with alfa-methyl-omega-hydroxy-poly(oxy-1,2-ethanediyl) and 2-methyl-2-propenoate, represented by CAS No. #[119724-54-8]. Other block copolymers with similar HLB values may be used as well.
3. The rest of the compounds must be selected after testing those already suggested, according to similar chemical and functional properties, and at the view of the examples.
4. The content in oil (namely of active ingredient(s) and eventually solvents) must be in a percentage of 30-60% wt.-% with respect to 100% of the oil and water phase together. Although values below 30% may be used when the concentration of the a.i. is low (e.g., in a final formulation wherein the a.l. is at 40 g/L), values over 60% show problems of emulsification and microencapsulation, that can be solved tough with repeated modifications of the total composition (in particular the selection of surfactants) in a trial-error basis. In particular, it is recommended that the active ingredient is present form minute quantities (>0%) till 45% wt.-% in the final formulation.
5. The influence in the present type of microencapsulation (urea formaldehyde resin+glycoluril resins) of the a.i. is low (at least we have not appreciated them). Thus, the substitution of an active ingredient by another one, even when the chemical structure is very different—but maintaining its lipophilic character—is a operation possible to be embodied. Not to mention that the biological function of the microencapsulated product plays in itself no role in the process; namely, the microencapsulated materials may have a pharmacological, insecticide, herbicide or fungicide activity, of to be catalysts, phase transfer materials, medicines, etc. What is important is that they are lipophilic and that they do not have labile groups that may be destroyed during the course of the process (situation that an skilled chemist may preview at first sight observing the chemical structure of the compound to be microencapsulated, as is the case for compounds that suffer immediate hydrolysis when in contact with water or that they are attacked by isocyanate or glycoluril groups or that they precipitate in the presence of polymers of pyrrolidone).
6. The quantity of active ingredients can be from traces till approximately 45% wt.-% with respect to the final formulation (that contains also the water). The expert shall substitute accordingly, in the formulations described in the examples, the a.i. by more solvent (if the aim is to reduce the concentration of a.i.). If the expert wants to obtain an increased concentration of the a.i. the solvent may be diminished or even removed as far the a.i. at least at atmospheric pressure and at the temperature of emulsification.
7. After the formulation is finished, it can be added to its water phase (wherein the capsules are dispersed in water) conventional additives to perform a spray-dry process and get afterwards dry formulations containing the microcapsules herein described (e.g., water dispersable granules) with a higher content in a.i. (e.g. 50-80%, due to the evaporation of water).
8. It is also possible to add to the final capsule suspension (CS) a suspension concentrate (SC) and then obtain a mix formulation of the type ZC in international code. The incorporation of the SC can be done without major problems by the skilled in formulation. In the same way, other types of formulation may be obtained from the CS formulations herein described in detail.
9. Modifications of the CS formulations may lead, for example to an emulsion concentrate (EC) mixed with a CS formulation, or to reformulated the microcapsules in an oil phase after drying such microcapsules.
10. When the water phase shows too high viscosity, it is possible to add part of the components of the water phase after the microencapsulation process, with the proviso that the emulsifying ability is maintained within the objective of microencapsulate (e.g., do not at the xanthan gum before microencapsulation and adding it at the end of the process).

Worthy to note, although the origin and the best realization of the invention corresponds to microencapsulation of compounds with at least a carboxamide group, the inventors have found that the same process and the same formulation ingredients (except the a.i.) may be used with excellent results, in particular the reduction of the agglomerates of the microcapsules and the reduction of material non-microencapsulated (that if it is non-soluble in water, crystallizes in the water phase, if we use other techniques state of the art). Since the formulation process is novel, and moreover, it provides advantages over state of the art microencapsulation methods, the skilled formulation chemist can apply this invention to many other agrochemical compounds, without the inventors knowing at the time of writing this document, no limitation in regard to any organic molecule used in agrochemistry (e.g., those described in the e-Pesticide Manual, 2003, ISBN 1-901396-34-7) that us water insoluble (highest solubility at room temperature 1 g/L). Even the present invention may bne used to microencapsulate catalysts, phase transfer materials, phase change materials (PCM), medicines, nutrients, etc.

EXAMPLES

Example 1

It is proceeded to perform a microencapsulation of the carboxamide fungicide flutolanil CAS No. #[6632-96-5], in order to finally obtain a formulation CS Flutolanil 360 g/L.

Syperonic® PE/L64 is a non-ionic emulsifier of the type block copolymer ethoxylated/propoxylated.

Ganex® P904L is a modified polymer of polyvinylpyrrolidone with unpolar character.

Atlox® 4913 is a non-ionic dispersant of the type block copolymer ABA

Two phases water and oil are prepared:

| Compound | wt-% |
| --- | --- |
| Water Phase: | |
| Synperonic ® PE/L64 | 2.0 |
| Ganex ® P904L (at 10%) | 35.00 |
| Goma xantana (50% in water at 80° C.) | 3.00 |
| Polyvinylalcohol PVP K-30 (20% in agua) | 2.60 |
| Ascorbic acid | 0.01 |
| Micronized aluminosilicates at 10% | 2.00 |
| Sodium salt of lignosulfonic acid | 0.49 |
| Atlox ® 4913 | 2.00 |
| Antifoaming silicon oil | 0.10 |
| p-TSA | 0.80 |
| Oil Phase | |
| Technical flutolanil | 34.50 |
| Solvesso ® 200 ND | 13.00 |
| Urea resin UFR ® 80 | 3.00 |
| Cymel ® 1170 | 1.00 |
| Atlox ® 4912 | 0.50 |
| TOTAL OIL PHASE + WATER PHASE | 100 |

Both phases are heated independently at 60° C. Once reached that temperature, it is checked that the pH of the water phase in the range 4-5.5 (and adjusted if necessary). Then the water phase is added to the oil phase while stirring and mixing with high shear stress at high speed (about 2500 rpm, sufficient to produce oil droplets below 5 μm). After 10-20 minutes, the high shear stress stirrer is changed to an anchor type at low speed (100-300 rpm). The reactor Is kept at 55° C. during 120-180 minutes and then it is left to cool down to room temperature.

The resulting formulation has the following characteristics__

Particle size (measured in a MasterSizer® equipment diluted in water): mean of 3.7 μm and percentile 90 of 17 μm.

Agglomeration of microcapsules after production and storage at 54° C. and 14 days: not appreciable upon microscopic observation.

Storage stability at 54° C. for 28 days: after this period, initially small agglomerations that after gentle agitation disappear. High dispersibility of the microcapsules (>90%) [without bleeding], meaning this that the shelf life of the formulation may be 3 or 4 years, well over the current shelf life of state of the art microencapsulated products.

According FAO specifications for CS formulations and CIPAC methods we obtain:

Wet sieve residue (75 pm): 0.07% wt.-%

Dispersibility of the microcapsules: 92%

Suspensibility of the microcapsules: 94%

Example 2

It is proceeded to perform a microencapsulation of the carboxamide flutolanil CAS No. #[6632-96-5], in order to finally obtain a formulation CS Prochloraz 360 g/L.

Antarox® B25 is a non-ionic emulsifier of the type block copolymer ethoxylated/propoxylated.

Ganex® V216 is a modified polymer of polyvinylpyrrolidone with unpolar character.

Reax® 88 is a salt of lignosulfonic acids.

Two phases water and oil are prepared:

| Compound | wt.-% |
| --- | --- |
| Water Phase: | |
| Antarox ® B25 | 2.00 |
| Ganex ® V216 (at 20%) | 40.00 |
| Goma guar (at 20% in water) | 1.00 |
| Polyvinylalcohol (20% in water) | 1.50 |
| Phosphoric acid (and NaOH for pH adjustment to pH = 6) | 0.01 |
| Micronized sepiolite in water at 1% | 1.00 |
| Sodium salt of lignosulfonic acid | 0.49 |
| Reax ® 88 | 2.00 |
| Antifoaming silicon oil | 0.10 |
| p-TSA | 0.80 |
| Oil Phase: | |
| Technical Prochloraz | 34.50 |
| Solvesso ® 200 ND | 13.00 |
| Urea resin UFR ® 80 | 2.10 |
| Cymel ® 1170 | 1.00 |
| Atlox ® 4912 | 0.50 |
| TOTAL OIL PHASE + WATER PHASE | 100 |

It is followed the process already disclosed in Example 1.

Comparative Examples

In a numerous series of experiments it was observed that the substitution of the glycoluril resins (Cymel® 1170, for example) by isocyanates state of the art or melamine formaldehyde condensate resins reacted too fast with carboxamide compounds. The use of Cymel® 1170 with isocyanates TDI and PMPPI (common names to designate such isocyanates) also provokes a faster reaction with respect with examples 1 and 2. Without the use of the copolymers CoP-1, the mean particle size is consistently over 5 μm, in particular 7-9 μm and through the agglomerated test for extended shelf life (28 days at 54° C.) they show agglomeration.

On the other hand, any tested formulation performed in the absence of copolymers CoP-1 (substituting them by Atlox® 4912) results in an agglomeration higher that that observed if CoP-1 are used. Although such formulations without CoP-1 may be acceptable for commercial uses, the extreme stability of the formulations according the present invention are not reached without the use of the wall forming material and the use of the CoP-1.

The invention claimed is:

1. A formulation of microcapsules, wherein the microcapsules encapsulate one or several chemical compounds, in aqueous suspension characterized in that:
   a) the wall of the microcapsules is formed by a polymer consisting of the reaction of:
      a.1) at least a glycoluril resin of the type N,N',N'',N'''-tetrakis(alkoxyalkyl)glycoluril, N,N'-bis(alkoxyalkyl)glycoluril or N,N',N''-tris(alkoxyalkyl)glycoluril;
      a.2) at least a urea formaldehyde resin of CAS No. #[9011-05-6], being the quantity of a.1) plus a.2) of 0.5-7.5 wt.-% with respect to the whole formulation;
   b), the water phase contains at least a polymeric compound selected from the group consisting of:
      b.1) polymers of N-vinyl-2-pyrrolidone with vinyl-1-alkenes and/or a polymer of 1-butene combined with N-vinyl-2-pyrrolidone; and optionally
      b.2) polymers of N-vynil-pyrrolidone with vinyl esters; and being present the compound(s) b.1) plus b.2) at 1-15 wt.-% with respect to the total weight of the formulation; and
   c) the microcapsules have a mean particle size of 1-6 µm.

2. The formulation containing microcapsules according to claim 1 characterized in that in the aqueous phase there are present, at 0.5-7 wt.-%, dispersants of lignosulfonate salts or lignosulfonate.

3. The formulation containing microcapsules according to claims 1 or 2, characterized in that at least one compound enclosed in the microcapsules is an agrochemical compound comprises at least a carboxamide group.

4. The formulation containing microcapsules according to claim 3 characterized in that the at least one microencapsulated compounds or several compounds is/are selected from the group consisting of: boscalid, prochloraz, flutolanil, furametpyr, mepronil, oxycarboxin and thifluzamide.

5. The formulation containing microcapsules according claim 3 characterized in that the compounds to be microencapsulated are chosen, at least one of them, or several of them, from the group of sulfonylureas.

6. The formulation of microcapsules according claim 1 characterized in that:
   a) the chemical compound is selected from the group consisting of: boscalid, prochloraz, carboxin, fenfuran, flutolanil, furametpyr, mepronil, oxycarboxin, thifluzamide, sulfonylureas; and is present at a concentration 0.1-45 wt.-%
   b) the aqueous phase contains:
      i) at least a vinylpyrrolidone/vinylalkene polymer compound
      ii) an emulsifier of the type block copolymer ethoxylated/propoxylated
      iii) a dispersant that is a derivative of lignosulfonic acids
      iv) polymers of polyvinyl alcohol and/or polyvinyl pyrrolidone, without derivatization of such structures
      v) a gum of biological origin
      vi) a sulfonic acid
      viii) an antifoam
      ix) optionally a microbiological protector
      x) as needed, pH stabilizers or buffer solutions
   c) the oil phase contains:
      i) the chemical compound cited in a)
      ii) a solvent of the type vegetable oil or fat, animal oil or fat or petroleum derivative
      iii) an emulsifier of the type block copolymer ABA of polyethylenglycol and fatty acid with a carbon chain of at least 12 carbon atoms
      iv) optionally, antioxidants and/or ultraviolet or visible light protectors
   d) the wall of the microcapsules is formed by a polymer consist of a reaction product of a urea resin and a glycoluril resin, such reaction catalyzed by the presence of water and a sulfonic acid and in absence of any other type of catalysts
   e) the mean size of the microcapsules is 1-6 µm.

7. The formulation according claim 6 characterized in that the chemical compound is prochloraz and it is present in the formulation at a concentration 5-40 wt.-%.

8. A process of production of microcapsules of claim 1 by means of in-situ polymerization characterized in that:
   a) the oil phase that is emulsified in the water phase contains, coformulants, as well as wall forming materials consisting of:
      a.1) at least a glycoluril resin of the type N,N',N'',N'''-tetrakis(alkoxyalkyl)glycoluril, N,N'-bis(alkoxyalkyl)glycoluril or N,N',N''-tris(alkoxyalkyl)glycoluril; and
      a.2) at least a urea formaldehyde resin with CAS No. #[9011-05-6], being the quantity of a.1) plus a.2) of 0.5-7.5 wt.-% with respect to the whole formulation;
   b) the water phase contains, coformulants, as well as at least a polymer from the group consisting of:
      b.1) polymers of N-vinyl-2-pyrrolidone with vinyl-1-alkenes and/or polymers of 1-butene combined with N-vinyl-2-pyrrolidone; and optionally
      b.2) polymers of N-vinyl-pyrrollidone with vinyl esters; and
   being present the compound(s) b.1) plus b.2) at 1-15 wt.-% with respect of the total weight of the formulation; and
   c) stirring at a speed, with quantities of compounds b) present, needed to obtain a mean particle size of 1-6 µm and performing the steps of the process:
      i) preparing a water phase containing emulsifiers and coformulants and compounds b), and optionally, a polyamine or polyol;
      ii) preparing of an oil phase containing the chemical compound(s) to be microencapsulated, compounds a) and a catalyst of the sulfonic acid type,
      iii) emulsifying the oil phase into the water phase at a temperature of 46-90° C. under high shear stress stirring for an amount of time necessary to achieve the desired mean particle size; and
      iv) replacing the high shear stress stirrer by another stirrer for mild agitation and curing of the formed microcapsules until the temperature of the microcapsules reaches 30-40° C. by non-forced cooling down to room temperature.

9. Microcapsules characterized in that the polymer that forms their wall consist of a mixed polymer resulting from the reaction of a urea resin characterized by the CAS No. #[9011-05-6] and a glycoluril resin containing N,N',N'',N'''tetrakis(butoxymethyl)glycoluril.

10. Method that is beneficial for the agriculture and for animal or plant protection comprising:
   a) producing microcapsules according to the claim 9
   b) formulate such microcapsules in any suitable form for its use in agriculture, or such capsule suspension combined with an emulsifiable concentrate or combined with a suspension concentrate, water dispersable granules, sprays or powders c) applying it to plants or to the animals by any known method in agriculture or animal farming.

11. Method of elimination of any pest, including those pests that are animals, plants, fungi and microorganisms, in agriculture and animal farming, comprising:
   a) producing a formulation of microcapsules according to claims 1 or 2
   b) applying such formulation to target places of interest by means of spraying a water solution in which the formulation of microcapsules according to a) has been previously diluted.

* * * * *